United States Patent [19]
Seido et al.

[11] Patent Number: 5,859,249
[45] Date of Patent: Jan. 12, 1999

[54] 2-PHENYL-2-(2'-PIPERIDINYLIDENE) ACETATE DERIVATIVE, PROCESS FOR MANUFACTURING THE SAME, AND PROCESS FOR MANUFACTURING OPTICALLY ACTIVE 2-PHENYL-2-(2'-PIPERIDINYL)ACETATE DERIVATIVE BY ASYMMETRICALLY HYDROGENATING THE SAME

[75] Inventors: Nobuo Seido; Takenobu Nishikawa; Tsukasa Sotoguchi; Yoshifumi Yuasa; Takashi Miura; Hidenori Kumobayashi, all of Kanagawa, Japan

[73] Assignee: Takasago International Corporation, Tokyo, Japan

[21] Appl. No.: 895,428

[22] Filed: Jul. 16, 1997

[30] Foreign Application Priority Data

Feb. 19, 1997 [JP] Japan .................................. 9-072570
Apr. 2, 1997 [JP] Japan .................................. 9-117358

[51] Int. Cl.$^6$ ........................ C07D 211/02; C07D 211/32
[52] U.S. Cl. ............................ 546/235; 560/60; 502/208
[58] Field of Search ............................ 546/235; 560/60; 502/208

[56] References Cited

PUBLICATIONS

Gluchowski et al. "Preparation of dihydropyridine derivatives as drugs" CA 123:143638, 1994.

*Primary Examiner*—Ceila Chang
*Attorney, Agent, or Firm*—Sughrue, Mion, Zinn, Macpeak & Seas, PLLC

[57] ABSTRACT

Disclosed is a 2-phenyl-2-(2'-piperidinylidene)acetate derivative suitably used for a raw material of a 2-phenyl-2-(2'-piperidinyl)acetate derivative and a process for manufacturing the same. Also disclosed is a process for manufacturing an optically active 2-phenyl-2-(2'-piperidinyl) acetate derivative which is a major intermediate for an antidepressant. The 2-phenyl-2-(2'-piperidinylidene)acetate derivative is manufactured by cyclizing a 7-(N-substituted amino)-3-oxo-2-heptanoate derivative. The optically active 2-phenyl-2-(2'-piperidinyl)acetate derivative is manufactured by asymmetrically hydrogenating the 2-phenyl-2-(2'-piperidinylidene)acetate derivative in the presence of a complex of a Group VIII transition metal or an acid.

7 Claims, No Drawings

2-PHENYL-2-(2'-PIPERIDINYLIDENE) ACETATE DERIVATIVE, PROCESS FOR MANUFACTURING THE SAME, AND PROCESS FOR MANUFACTURING OPTICALLY ACTIVE 2-PHENYL-2-(2'-PIPERIDINYL)ACETATE DERIVATIVE BY ASYMMETRICALLY HYDROGENATING THE SAME

BACKGROUND OF THE INVENTION

1. Field of the Invention

The present invention relates to a novel 2-phenyl-2-(2'-piperidinylidene)acetate derivative and a process for manufacturing the same. This derivative is useful as a raw material for manufacturing an optically active 2-phenyl-2-(2'-piperidinyl)acetate derivative which is the major intermediate of an antidepressant as described below. The present invention also relates to a process for manufacturing an optically active 2-phenyl-2-(2'-piperidinyl)acetate derivative which is a major intermediate of an antidepressant.

2. Description of the Related Art

As an antidepressant, methyl threo-2-phenyl-2-(2'-piperidinyl)acetate/hydrochloride (Trade name: Ritalin) is commercially available in the form of racemic compounds. Also, it is known for this antidepressant that a specific stereoisomer has a pharmacological activity five times higher than that of other stereoisomers (see U.S. Pat. No. 2,957,880).

Further structural analysis studies on methyl 2-phenyl-2-(2'-piperidinyl)acetate have progressed and the absolute configuration of the optically active form of this compound has been reported (see J. Med. Chem., 12, 266, 1969).

The above optically active methyl 2-phenyl-2-(2'-piperidinyl)acetate is manufactured, for example, by the following known processes:

(1) A process in which phenylacetonitrile and 2-chloropyridine are condensed in the presence of sodium amide, followed by hydrolysis and a reduction to prepare 2-phenyl-2-(2'-piperidinylidene)acetic acid amide (see U.S. Pat. No. 2,507,361). A threo compound is then prepared by a recrystallization of that acid amide. The threo compound is then optically resolved using optically active tartaric acid, followed by hydrolysis and an esterification reaction to synthesize the above optically active compound (see U.S. Pat. No. 2,957,880).

(2) A process in which optically active chlorophenylamine is subjected to a Hofmann decomposition reaction to prepare an olefinic compound, which is then subjected to an oxidation reaction using ozone to synthesize the above optically active compound (see J. Pharm. Sci, 56, 1689, 1967).

However, in these processes, complicated operations are required and it is also necessary to use an expensive reagent for optical resolution and/or to use an optically active compound.

SUMMARY OF THE INVENTION

An object of the present invention is to provide a novel compound and a process for manufacturing the novel compound.

Another object of the present invention is to provide a means for synthesizing an optically active 2-phenyl-2-(2'-piperidinyl)acetate derivative simply and at low cost.

The present invention provides a 2-phenyl-2-(2'-piperidinylidene)acetate derivative represented by the following formula (1):

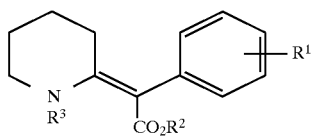

wherein $R^1$ represents a hydrogen atom, a lower alkyl group having 1 to 4 carbon atoms, or a lower alkoxy group having 1 to 4 carbon atoms; $R^2$ represents a lower alkyl group having 1 to 4 carbon atoms; and $R^3$ represents a hydrogen atom or a protective group for an amino group, a process for manufacturing the 2-phenyl-2-(2'-piperidinylidene)acetate derivative; and a process for manufacturing a 2-phenyl-2-(2'-piperidinyl)acetate derivative represented by the following formula (3):

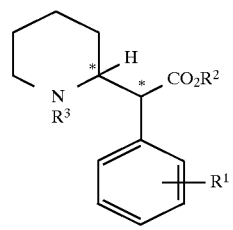

wherein $R^1$, $R^2$ and $R^3$ are the same groups as defined above and * represents an asymmetrical carbon atom, which process comprises the steps of: asymmetrically hydrogenating, in the presence of a complex of a group VIII transition metal, a 2-phenyl-2-(2'-piperidinylidene)acetate derivative represented by the following formula (1):

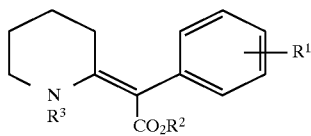

wherein $R^1$, $R^2$ and $R^3$ are the same groups as earlier defined.

DETAILED DESCRIPTION OF THE INVENTION

In the compounds represented by the formula (1), examples of the lower alkyl group represented by $R^1$ include a methyl group, ethyl group, propyl group, and the like; and examples of the lower alkoxy group include a methoxy group, ethoxy group, propoxy group, and the like. As examples of the lower alkyl groups represented by $R^2$ there are a methyl group, ethyl group, propyl group, and the like. Examples of the protective groups for the amino group represented by $R^3$ include a benzyl group, benzyloxycarbonyl group, lower alkoxycarbonyl group having 1 to 4 carbon atoms, t-butyldimethylsilyl group, allyl group, and the like. The $R^1$ is preferably substituted at para-site.

The preferred compound has a hydrogen atom as the $R^1$, a methyl group as the $R^2$ and a hydrogen atom as the $R^3$.

The above compounds of formula (1) can be produced by cyclizing 7-(N-substituted amino)-3-oxo-2-phenyl heptanoate represented by the following formula (2):

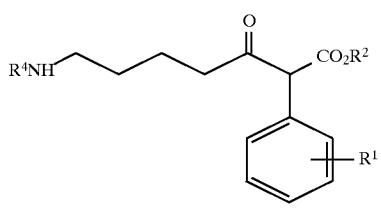

(2)

wherein $R^1$ and $R^2$ are the same groups as earlier defined and $R^4$ represents a protective group for an amino group.

The compound represented by formula (2) can be produced, for example, by the following process:

First, an imidazolide compound of 5-N substituted aminopentanoic acid is prepared using 5-N substituted aminopentanoic acid and N,N'-carbonyldiimidazole (hereinafter referred to as "CDI").

An enolate compound of phenylacetate is prepared using phenylacetate and lithium diisopropylamide.

Using the imidazolide compound and the enolate compound, 7-(N-substituted amino)-3-oxo-2-phenyl heptanoate of formula (2) is prepared.(B. D. Havvis, M. M. Jonllie, Tetrahedron Lett. 1987, 28, 2837)

The compound represented by formula (1) can be produced by cyclizing the 7-(N-substituted amino)-3-oxo-2-phenyl heptanoate of formula (2).

Preferred processes for manufacturing the compound represented by formula (1) are:

(a) A process in which a protective group for an amino group is removed (hereinafter referred to as "protection removal") from the compound represented by formula (2) and the resulting compound is reacted to combine the carbon atoms at the third position and at the seventh position thereof to produce the compound represented by formula (1);

(b) A process in which the protection removal and the reaction of combining the carbon atoms at the third and the seventh positions of the compound represented by formula (2) progresses simultaneously to produce the compound represented by formula (1) in one step; and (c) A process in which only the reaction of combining the carbon atoms at the third and the seventh positions of the compound represented by formula (2) is carried out to produce the compound represented by formula (1).

The compound represented by formula (1) can also be prepared by substituting the hydrogen atom combined with the nitrogen atom of the compound prepared in the above process (a) or (b) with another functional group, and further substituting the group represented by $R^4$.

Illustrating preferred embodiments further, in process (a) the compound represented by formula (2) in which the protective group of the amino group is a t-butoxycarbonyl group is used as a starting compound. The protection removal of the starting compound is first carried out and then the resulting product is cyclized under alkaline conditions to produce the compound represented by formula (1).

In process (b), the compound represented by formula (2) in which the protective group of the amino group is a benzyloxycarbonyl group is used as the starting compound. The protection removal of the starting compound is first carried out and then the resulting product is cyclized in the presence of a palladium-carbon (Pd—C) catalyst to produce the compound represented by formula (1).

More specifically, in process (a) the starting compound is first dissolved in a solvent and mixed with stirring to carry out the protection removal.

As the solvent, lower alcohols having 1 to 4 carbon atoms such as methanol, ethanol, butanol, or the like; or fatty acid lower alkyl esters having 1–4 carbon atoms such as methyl acetate, ethyl acetate, butyl acetate or the like can be used. The alcohols as mentioned above are preferred, and methanol is more preferred.

The solvent is selected to dissolve the starting compound in a range from 1 to 20% by weight based on the solvent. The reaction is carried out generally at room temperature to 100° C., preferably at room temperature to 50° C., generally for 2 to 18 hours.

At the protection removal reaction, it is desirable to add an acid in a proportion of from 1 to 20 mols per 1 mol of the starting compound, because the acid brings about desirable results, for example, the protection removal proceeds smoothly.

Examples of the acid include mineral acids such as hydrochloric acid, sulfuric acid, nitric acid, phosphoric acid, and the like; and organic acids such as organic carboxylic acids, organic sulfonic acids, and the like. These compounds may be used either alone or in combinations of two or more. Among these, hydrochloric acid is most preferred.

Cyclization of the reaction product is next carried out.

It is desirable to use the same solvent as used in the protection removal reaction for cyclization. The proportion of the solvent is from 1 to 20% by weight based on the starting compound.

The cyclization reaction is preferably carried out with stirring at a temperature of from room temperature to 50° C., although the cyclization reaction may be carried out at a temperature of from room temperature to 100° C., and generally is carried out for 2–18 hours.

For the cyclization reaction, it is desirable to add a base in a proportion from 1 to 5 by mols based on the starting compound, because such amount of the base brings about desirable results, for example, the cyclization reaction is promoted.

As examples of the base there are carbonates such as sodium carbonate, potassium carbonate, calcium carbonate, and the like; triethylamine, ethyldiisopropylamine, dimethylaniline, pyridine, N-methylpyridine, and the like. These compounds may be used either alone or in combinations of two or more. Among these, potassium carbonate is most preferred.

The above process (b) is specifically as follows:

The starting compound is dissolved in a solvent and reacted in the presence of a catalyst under a hydrogen atmosphere. The pressure of thr $H_2$ atmosphe is in the range of from 1 to 50 atmospher, preferably from 1 to 20 atomospher.

As the solvent, a lower alcohol having 1 to 4 carbon atoms such as methanol, ethanol, butanol, or the like; or a fatty acid lower alkyl ester such as ethyl acetate or the like is used. The alcohols as mentioned above are preferred, and especially methanol is preferred.

The solvent is selected to contain the starting compound in a range from 1 to 20% by weight based on the weight of the solvent, preferably from 5 to 20% by weight.

As the catalyst, a palladium-carbon type catalyst is particularly preferred. The catalyst is used in a range from 0.1 to 50% by weight, preferably from 1 to 10% by weight, based on weight of the starting compound.

The reaction is preferably carried out at a temperature of from room temperature to 50° C., although the reaction may be conducted at a temperature of from room temperature to 100° C., and generally is carried out for from 2 to 18 hours. Cyclization is then conducted as earlier described.

The compound represented by formula (1) prepared in the above manner is thus asymmetrically hydrogenated in the presence of a complex of a Group VIII transition metal which comprises an optically active phosphine as a ligand to prepare the optically active 2-phenyl-2-(2'-piperidinyl) acetate represented by the following formula (3):

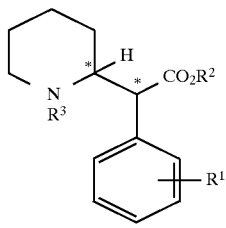
(3)

wherein $R^1$, $R^2$, and $R^3$ are the same groups as defined above.

These 2-phenyl-2-(2'-piperidinyl)acetates include four stereoisomers as shown in Table 1.

TABLE 1

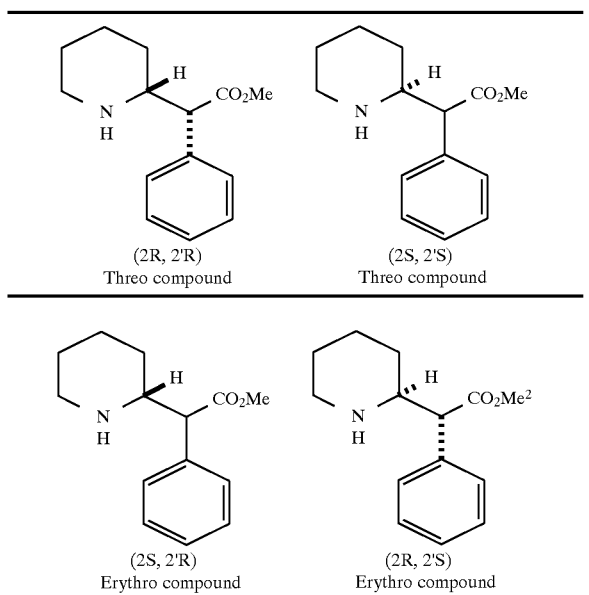

| (2R, 2'R) | (2S, 2'S) |
| Threo compound | Threo compound |
| (2S, 2'R) | (2R, 2'S) |
| Erythro compound | Erythro compound | wherein Me represents a methyl group.

In the present invention, although all these stereoisomers can be produced, it is particularly easy to produce the erythro compound, (2S, 2'R)-2-phenyl-2-(2'-piperidinyl) acetate derivative, represented by the following formula (5):

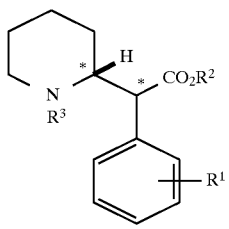
(5)

wherein $R^1$, $R^2$ and $R^3$ are the same groups as earlier defined.

The complexes of the Group VIII transition metal used in the present invention include the following compounds.

Preferred complexes represent compounds having the following formula (4):

$$M_m L_n X_q Q_r Y_s \quad (4)$$

wherein M represents a ruthenium atom, iridium atom, or rhodium atom; L represents an optically active phosphine ligand; X represents a hydrogen atom, halogen atom or carboxylic acid derivative residue; Q represents ethylene, 1,5-octadiene, benzene, p-cymene, mesitylene, and the like; Y represents an anion selected from the group consisting of $ClO_4^-$, $BF_4^-$, and $PF_6^-$; m, n, and s respectively denote an integer of 1 or 2; r denotes an integer of 0 or 1; and q denotes an integer from 0 to 2 or denotes the integer 4.

The carboxylic acid derivative residue includes groups represented by the following formula (6):

$$R^5 CO_2 \quad (6)$$

wherein $R^5$ represents a lower alkyl group having 1–4 carbon atoms which may contain halogen atoms. Preferred examples include a methyl group, trifluoromethyl group, tribromomethyl group, or t-butyl group.

The complexes used in the present invention also include complexes having a coordinated group represented by the formula $NR^6R^7R^8$ furthermore, wherein $R^6$, $R^7$, and $R^8$ may be the same or different, and each represent a lower alkyl group having 1 to 4 carbon atoms; and two groups among $R^6$, $R^7$, and $R^8$ may form a heterocyclic ring in combination with the nitrogen atom.

Preferred examples of the compounds represented by the formula $NR^6R^7R^8$ are triethylamine, tributylamine, ethyldiisopropylamine, 1,8-bis(dimethylamino)naphthalene, dimethylaniline, pyridiene, N-methylpiperidine, and the like.

These transition metal complexes can be prepared according to known methods, for example, disclosed in Japanese Patent Application Laid-open No. 61-265239 or Experimental Chemistry Lecture (Fourth edition), Vol. 18, Organic metal complex, Page 327–367.

The complexes used in the present invention also include complexes obtained by adding a Lewis acid such as a metal halide to the above complexes with which the amine is coordinated, and agitating the resulting mixture.

Preferred examples of the metal halides include titanium tetrachloride, titanium tetrabromide, tin dichloride, iron trichloride, aluminum chloride, calcium chloride, samarium chloride, samarium iodide, lanthanum chloride, and cerium chloride.

Among the above complexes, particularly preferred are:

1) Complexes represented by the formula RuXY'(L), wherein X represents a hydrogen atom, halogen atom, or the carboxylic acid derivative residue; X' represents a halogen atom or the carboxylic acid derivative residue; and L represents an optically active phosphine ligand.

2) Complexes represented by the formula [RuX(L)Q]Y, wherein X, Y, L and Q are the same as earlier define.

3) Complexes represented by the formula [Ru$_2$Cl$_4$(L)$_2$] $NR^6R^7R^8$, wherein L, $R^6$, $R^7$, and $R^8$ are the same as earlier defined.

4) Complexes represented by the general formula [IrQ(L)]Y, wherein Y, L and Q are the same as earlier defined.

5) Complexes represented by the general formula [RhQ(L)]Y, wherein Y, L, and Q are the same as earlier defined.

In this invention, the complex is added to a reaction system to conduct a hydrogenation reaction. An alternative process may be employed in which components of the complex are mixed in advance or not mixed in advance and then added to a reaction system to be hydrogenated.

Specifically, one mol of [iridium (cyclooctadienyl) chloride]$_2$ (hereinafter abbreviated as "[Ir(COD)Cl]$_2$") or [rhodium (cyclooctadienyl) chloride]$_2$ (hereinafter abbreviated as "[Rh(COD)Cl]$_2$"), two mols of the optically active phosphine ligand, and a solvent are placed in an autoclave and agitated to prepare a complex.

Alternatively, a solvent such as methylene chloride, dichloropropane or the like is added to the complex of the formula $[Ru_2Cl_4(L)_2]NR^6R^7R^8$ in an amount from 5 to 10 times by weight based on the complex to dissolve the complex. To the solution is added from 1 to 5 mols of a metal halide, which is agitated at room temperature for 2 to 18 hours, followed by concentration under reduced pressure to prepare a mixed product. Preferred metal halides are compound described earlier.

Either of the identified complex is then added to a reaction system to perform a hydrogenating reaction.

As specific examples of the optically active phosphine ligand used in this process are (R)-2,2'-bis-(diphenylphosphino)-1,1'-binaphthyl (hereinafter abbreviated as "BINAP"), (R)-2,2'-bis-(di-p-tolylphosphino)-1,1'-binaphthyl (hereinafter abbreviated as "Tol-BINAP"), (R)-2,2'-bis-(di-p-chlorophenylphosphino)-1,1'-binaphthyl (hereinafter abbreviated as "p-Cl-BINAP"), 2,2'-bis (diphenylphosphino)-5,5',6,6', 7,7',8,8'-octahydro-1,1'-binaphthyl (hereinafter abbreviated as "H8-BINAP"), (R)-2,2'-bis-(di-3,5-xylylphosphino)-1,1'-binaphthyl (hereinafter abbreviated as "DM-BINAP"), (R)-2,2'-bis (dicyclohexylphosphino)-6,6'-dimethyl-1,1'-biphenyl (hereinafter abbreviated as "BICHEP"), (R)-2,2'-bis-(diphenylphosphino)-6,6'-dimethyl-1,1'-biphenyl (hereinafter abbreviated as "BIPHEMP"), (+)-2,2'-bis (diphenylphosphino)-4,4',6,6'-tetramethyl-5,5'-dichloro-1,1'-biphenyl (hereinafter abbreviated as "CM-BIPHEMP"), (R)-2-(dibiphenylphosphino)-2'-(diphenylphosphino)-1,1'-binaphthyl (hereinafter abbreviated as "BiPh-Ph-BINAP"), and (R)-2-(dicyclohexylphosphino)-2'-(diphenylphosphino)-1,1'-binaphthyl (hereinafter abbreviated as "Cy-Ph-BINAP").

As the transition metal of these complexes, a rhodium atom, ruthenium atom, iridium atom, or the like is preferably used. Among these, the ruthenium atom or the iridium atom is more preferred.

More specific examples of the useful transition metal complexes are shown in Table 2.

TABLE 2

RuXY'(L)

RuCl$_2$(BINAP), RuCl$_2$(Tol-BINAP), RuCl$_2$(p-Cl-BINAP),
RuCl$_2$(H8-BINAP), RuCl$_2$(DM-BINAP), RuCl$_2$(BICHEP),
RuCl$_2$(BIPHEMP), RuCl$_2$(CM-BIPHEMP), RuCl$_2$(BIPh-Ph-BINAP),
RuCl$_2$(Cy-Ph-BINAP),
RuBr$_2$(BINAP), RuBr$_2$(Tol-BINAP), RuBr$_2$(p-Cl-BINAP),
RuBr$_2$(H8-BINAP), RuBr$_2$(DM-BINAP), RuBr$_2$(BICHEP),
RuBr$_2$(BIPHEMP), RuBr$_2$(CM-BIPHEMP), RuBr$_2$(BIPh-Ph-BINAP),
RuBr$_2$(Cy-Ph-BINAP),
RuCl$_2$(BINAP), RuCl$_2$(Tol-BINAP), RuHCl(p-Cl-BINAP),
RuHCl(H8-BINAP), RuHCl(DM-BINAP), RuHCl(BICHEP),
RuHCl(BIPHEMP), RuHCl(CM-BIPHEMP), RuHCl(BIPh-Ph-BINAP),
RuHCl(Cy-Ph-BINAP),
Ru(OCOCH$_3$)$_2$(BINAP), Ru(OCOCH$_3$)$_2$(Tol-BINAP),
Ru(OAc)$_2$(p-Cl-BINAP), Ru(OCOCH$_3$)$_2$(H8-BINAP),
Ru(OCOCH$_3$)$_2$(DM-BINAP), Ru(OCOCH$_3$)$_2$(BICHEP),
Ru(OCOCH$_3$)$_2$(BIPHEMP), Ru(OCOCH$_3$)$_2$(CM-BIPHEMP),
Ru(OCOCH$_3$)$_2$(BIPh-Ph-BINAP), Ru(OCOCH$_3$)$_2$(Cy-Ph-BINAP),
Ru(OCOCF$_3$)$_2$(BINAP), Ru(OCOCF$_3$)$_2$(Tol-BINAP),
Ru(OCOCF$_3$)$_2$(p-Cl-BINAP), Ru(OCOCF$_3$)$_2$(H8-BINAP),
Ru(OCOCF$_3$)$_2$(DM-BINAP), Ru(OCOCF$_3$)$_2$(BICHEP),
Ru(OCOCF$_3$)$_2$(BIPHEMP), Ru(OCOCF$_3$)$_2$(CM-BIPHEMP),
Ru(OCOCF$_3$)$_2$(BIPh-Ph-BINAP), Ru(OCOCF$_3$)$_2$(Cy-Ph-BINAP),
[RuX(L)Q]Y

[RuCl(benzene)(BINAP)]Cl, [RuCl(benzene)(Tol-BINAP)]Cl,
[RuCl(benzene)(p-Cl-BINAP)]Cl, [RuCl(benzene)(H8-BINAP)]Cl,
[RuCl(benzene)(DM-BINAP)]Cl, [RuCl(benzene)(BICHEP)]Cl,
[RuClbenzene)(BIPHEMP)]Cl, [RuCl(benzene)(CM-BIPHEMP)]Cl, TABLE 2-continued

[RuCl(benzene)(BIPh-Ph-BINAP)]Cl, [RuCl(benzene)(Cy-Ph-BINAP)]Cl,
[RuI(p-cymene)(BINAP)]I, [RuI(p-cymene)(Tol-BINAP)]I,
[RuI(p-cymene)(p-Cl-BINAP)]I, [RuI(p-cymene)(H8-BINAP)]I,
([RuI(p-cymene)(DM-BINAP)]I, [RuI(p-cymene)(BICHEP)]I,
[RuI(p-cymene)(BIPHEMP)]I, [RuI(p-cymene)(CM-BIPHEMP)]I,
[RuI(p-cymene)(BIPh-Ph-BINAP)]I, [RuI(p-cymene)(Cy-Ph-BINAP)]I
[Ru$_2$Cl$_4$(L)$_2$]NR$^6$R$^7$R$^8$ {Ru$_2$Cl$_4$(BINAP)$_2$}NEt$_3$, {Ru$_2$Cl$_4$(Tol-BINAP)$_2$}NEt$_3$,
{Ru$_2$Cl$_4$(Cl-BINAP)$_2$}NEt$_3$, {Ru$_2$Cl$_4$(H8-BINAP)$_2$}NEt$_3$,
{Ru$_2$Cl$_4$(DM-BINAP)$_2$}NEt$_3$, {Ru$_2$Cl$_4$(BICHEP)$_2$}NEt$_3$,
{Ru$_2$Cl$_4$(BIPHEMP)$_2$}NEt$_3$, {Ru$_2$Cl$_4$(CM-BIPHEMP)$_2$}NEt$_3$
[IrQ(L)]Y

[Ir(COD)(BINAP)]Cl, [Ir(COD)(Tol-BINAP)]Cl,
[Ir(COD)(Cl-BINAP)]Cl, [Ir(COD)(H8-BINAP)]Cl,
[Ir(COD)(DM-BINAP)]Cl, [Ir(COD)(BICHEP)]Cl,
[Ir(COD)(BIPHEMP)]Cl, [Ir(COD)(CM-BIPHEMP)]Cl,
[Ir(COD)(BIPh-Ph-BINAP)]Cl, [Ir(COD)(Cy-Ph-BINAP)]Cl,
[Ir(COD)(BINAP)]ClO$_4$, [Ir(COD)(Tol-BINAP)]ClO$_4$,
[Ir(COD)(BINAP)]BF$_4$, [Ir(COD)(Tol-BINAP)]BF$_4$,
[Ir(COD)(BINAP)]PF$_6$, [Ir(COD)(Tol-BINAP)]PF$_6$
[RhQ(L)]Y

[Rh(COD)(BINAP)]Cl, [Rh(COD)(Tol-BINAP)]Cl,
[Rh(COD)(Cl-BINAP)]Cl, [Rh(COD)(H8-BINAP)]Cl,
[Rh(COD)(DM-BINAP)]Cl, [Rh(COD)(BICHEP)]Cl,
[Rh(COD)(BIPHEMP)]Cl, [Rh(COD)(CM-BIPHEMP)]Cl,
[Rh(COD)(BIPh-Ph-BINAP)]Cl, [Rh(COD)(Cy-Ph-BINAP)]Cl,
[Rh(COD)(BINAP)]ClO$_4$, [Rh(COD)(Tol-BINAP)]ClO$_4$,
[Rh(COD)(BINAP)]BF$_4$, [Rh(COD)(Tol-BINAP)]BF$_4$,
[Rh(COD)(BINAP)]PF$_6$, [Rh(COD)(Tol-BINAP)]PF$_6$

In the present invention, the above transition metal complexes are used in a molar amount of from 1/100 to 1/10,000 times, preferably from 1/200 to 1/1,000 times, one mol of the compound of formula (1) to permit the asymmetrical hydrogenating reaction to proceed smoothly and to prepare an asymmetrically hydrogenated product with higher chemical purities and optical purities.

The asymmetrical hydrogenating reaction is generally carried out at −30° C. to 250° C., preferably at 15° C. to 100° C., and under a hydrogen atmosphere of from 1 to 200 atmospher, preferably from 10 to 100 atmosphere.

The asymmetrical hydrogenation reaction is generally carried out in a solvent. Examples of the solvent include protic solvents such as methanol, ethanol, propanol, 2-propanol, and the like; and aprotic solvents such as methylene chloride, dichloroethane, tetrahydrofuran, dioxane, dimethoxyethane, dimethylformamide, dimethylsulfoxide, benzene, toluene, acetone, ethyl acetate, and the like. These solvents may be used either alone or in combinations of two or more. In the present invention, methanol is most preferred as the solvent.

The solvent is designed to dissolve and contain the compound of formula (1) In a range from 1 to 50% by weight, preferably from 3 to 10% by weight based on the solvent weight.

In the present invention, an acid is preferably added to the asymmetric hydrogenation reaction system to promote the reaction rate and to improve asymmetric selectivity. Examples of the acid used include mineral acids such as hydrochloric acid, sulfuric acid, nitric acid, phosphoric acid, and the like; and organic acids such as organic carboxylic acids, organic sulfonic acids, and the like. These acids may be used either alone or in combinations of two or more. Among these, hydrochloric acid or a mixture of hydrochloric acid and an other acid is most preferable.

The acid may directly added to the reaction system, or may also be added to the reaction system after the acid is mixed with a solvent.

The proportion of the acid is from 1/10 to 5 mols, preferably from 0.7 to 1.2, based on one mol of the compound of formula (1).

The hydrogenated reaction product may be directed to the next step, for example an epimerization reaction, without any treatment. It is preferred that purified hydrogenation reaction product is applied in the next step to increase the content of a desired optically active compound.

Conventionally known processes may be employed for this purifying treatment.

EXAMPLES

The present invention will be explained in more detail by way of examples, which are not intended to be limiting of the present invention. Apparatuses used for measuring material properties in each example are as follows:

Nuclear magnetic resonance: $^1$H-NMR; AM400 (400 MHz) (manufactured by Bruker Co., Ltd), $^{13}$C-NMR; AM400 (100 MHz) (manufactured by Bruker Co., Ltd.);

High performance liquid chromatography (HPLC): LC-7000 series (manufactured by Hitachi, Ltd.);

Mass spectrometry (MASS): M-80B (manufactured by Hitachi, Ltd.);

Melting point: MP-500D (manufactured by Yanaco Co., Ltd.).

Example 1
Synthesis of methyl 2-phenyl-2-(2'-piperidinylidene)acetate 31.8 g (83 mmol) of methyl 7-(N-benzyloxycarbonyl) amino-3-oxo-2-phenylheptanoate and 260 ml of methanol were mixed in a 1 liter autoclave while stirring to prepare a solution. 5.2 g of 5% Pd—C (5% Pd by weight based on the weight of the C; hereinafter the same) was added to the solution and the mixture was reacted at room temperature under a hydrogen pressure of 10 kg/cm$^2$ for 4 hours. The reaction solution was analyzed by HPLC to confirm the complete consumption of the raw material. The Pd—C was then separated by filtration using Celite. The filtrate was concentrated under reduced pressure. 60 ml of methanol was added to the residue, which was then allowed to stand at −25° C. overnight to recrystallize. The resulting precipitated non-colored crystals were separated by filtration and dried under reduced pressure to obtain the target compound in an amount of 18.02 g (93.9% yield). Analytical results on the target compound are given below.

m.p.: 115°~117° C.
$^1$H-NMR (CDCl$_3$/Me$_4$Si) δ:1.56(m,2H), 1.73(m, 2H), 2.11(t, J=6.5 Hz, 2H), 3.38(m,2H), 3.55(s,3H), 7.13(m,2H), 7.23(m,3H), 9.71(br,1H)
$^{13}$C-NMR (CDCl$_3$) δ: 19.96, 22.32, 27.78, 41.41, 50.48, 94.59, 126.01 127.91, 132.38, 138.24, 161.40, 170.39
Mass m/z: 231 (M+), 198, 170, 143, 115, 84, 55
Analytical conditions: (HPLC)
Column: Inertsil ODS-2 (GL Science Co., Ltd.)
Eluent: acetonitrile/water=7/3 by volume
Flow rate: 0.5 ml/min
Detector: UV=254 nm

Example 2
Synthesis of methyl 2-p-tolyl-2-(2'-piperidinylidene)acetate 5.0 g (12.6 mmol) of methyl 7-(N-benzyloxycarbonylamino)-3-oxo-2-p-tolylheptanoate and 260 ml of methanol were mixed in an 100 ml autoclave while stirring to prepare a solution. 250 mg of 5% Pd—C was added to the solution and the mixture was reacted at room temperature under a hydrogen pressure of 10 kg/cm$^2$ for 4 hours. The reaction solution was analyzed by HPLC to confirm the complete consumption of the raw material. Then, Pd—C was separated by filtration using Celite. The filtrate was concentrated under reduced pressure. 3 ml of methanol and 3 ml of hexane were added to the residue, which was then allowed to stand at −25° C. overnight to recrystallize. The resulting precipitated non-colored crystals were separated by filtration and dried under reduced pressure to obtain the target compound in an amount of 934 mg (30.3% yield). Analytical results on the target compound are given below.

m.p. 52.0°~52.8° C.
$^1$H-NMR (CDCl$_3$/Me$_4$Si) δ:1.57(m,2H), 1.72(m, 2H), 2.12(t, J=6.6 Hz, 2H), 2.34(s,3H) 3.36(m,2H), 3.55(s,3H), 7.00(m, 2H), 7.10(m, 2H), 9.70(br, 1H) $^{13}$C-NMR (CDCl$_3$) δ:19.99, 21.21, 22.35, 41.42, 50.49, 94.25, 128.7 3, 132.17, 135.15, 135.48, 161.43, 170.53
Mass m/z : 245 (M+), 212, 198, 170, 142, 115, 84, 55

Example 3
Synthesis of methyl 2-p-methoxyphenyl-2-(2'-piperidinylidene)acetate g (12.1 mmol) of methyl 7-(N-benzyloxycarbonylamino)-3-oxo-2-p-methoxyphenylheptanoate and 25 ml of isopropanol were mixed in an 100 ml autoclave while stirring to prepare a solution. 250 mg of 5% Pd—C was added to the solution and the mixture was reacted at room temperature under a hydrogen pressure of 20 kg/cm$^2$ for 4 hours. The reaction solution was analyzed by HPLC to confirm the complete consumption of the raw material. The Pd—C was then separated by filtration using Celite. The filtrate was concentrated under reduced pressure. 3 ml of methanol was added to the residue, which was then allowed to stand at −25° C. overnight to recrystallize. The precipitated non-colored crystals were separated by filtration and dried under reduced pressure to obtain the target compound in an amount of 1.71 g (54.3% yield). Analytical results on the target compound are given below.

m.p. 87.5°~88.5° C.
$^1$H-NMR (CDCl$_3$/Me$_4$Si) δ: 1.51(m,2H), 1.71(m,2H), 2.11(t,J=6.5 Hz,2H), 3.55(s,3H), 3.80(s,3H), 6.85(m,2H), 7.02(m,2H), 9.70(br,1H)
$^{13}$C-NMR (CDCl$_3$) δ:20.02, 22.34, 27.80, 41.42, 50.50, 55.12, 93.83, 113.39, 130.43, 133.24, 157.85, 161.60, 170.61
Mass m/z: 261 (M+), 228, 213, 200, 186, 173, 144, 121, 82

Example 4
Synthesis of t-butyl 2-phenyl-2-(2'-piperidinylidene)acetate 3.0 g (7.06 mmol) of t-butyl 7-(N-benzyloxycarbonylamino)-3-oxo-2-phenylheptanoate and 15 ml of methanol were mixed in an 100 ml autoclave while stirring to prepare a solution. 150 mg of 5% Pd—C was added to the solution and mixture was reacted at room temperature under a hydrogen pressure of 10 kg/cm$^2$ for 4 hours. The reaction solution was analyzed by HPLC to confirm the complete consumption of the raw material. The Pd—C was then separated by filtration using Celite. The filtrate was then concentrated under reduced pressure. The residue was purified by silica gel column chromatography (eluent: hexane/ethylacetate=6/1 by volume) to obtain the target compound as a non-colored oil in an amount of 1.04 g (yield: 53.8%). Analytical results on the target compound are given below.

$^1$H-NMR (CDCl$_3$/Me$_4$Si) δ:1.34(s,9H), 1.56(m,2H), 1.73 (m,2H), 2.13(t,J=6.5 Hz, 2H), 3.34(m,2H), 7.08(m,2H), 7.25(m.2H), 9.64(br, 1H)

$^{13}$C-NMR (CDCl$_3$) δ:19.20, 20.13, 22.45, 25.85, 27.90, 27.96, 28.09, 28.37, 28.55, 41.33, 96.64, 125.30, 126.67, 127.40, 132.31, 139.05, 160.36, 170.35

Mass m/z: 273 (M+), 217, 198, 188, 170, 143, 115, 105, 57

Example 5

Synthesis of methyl 2-phenyl-2-(2'-piperidinylidene)acetate 1 g (2.86 mmol) of methyl 7-(N-t-butoxycarbonylamino)-3-oxo-2-phenylheptanoate was placed in an 50 ml eggplant-shaped flask, and 5 ml of methanol and 5 ml of 3N hydrochloric acid were added thereto. The mixture was stirred at room temperature for 16 hours. After the dissipation of the peak of the raw material was confirmed by HPLC, the reaction solution was concentrated under reduced pressure to provide a residue. Then, 5 ml of methanol and 790 mg (5.72 mmol) of potassium carbonate were added to the residue and the resulting mixture was agitated at room temperature for 18 hours to give a reaction solution. The resulting reaction solution was concentrated under reduced pressure, and 20 ml of ethyl acetate and 5 ml of water were added thereto. The resulting mixture was transferred to a separatory funnel and extracted. After the separated organic layer was washed with 5 ml of saturated brine, the organic layer was dried with 3 g of magnesium sulfate anhydride, separated by filtration, and concentrated under reduced pressure. To the resulting residue was added 2 ml of methanol and the mixture was allowed to stand at −25° C. overnight to recrystallize. The precipitated non-colored crystals were separated by filtration and dried under reduced pressure to obtain the target compound in an amount of 420 mg (60.9% yield).

Example 6

Synthesis of ethyl 2-phenyl-2-(2'-piperidinylidene)acetate 1 g (2.86 mmol) of ethyl 7-(N-t-butoxycarbonylamino)-3-oxo-2-phenylheptanoate was placed in an 50 ml eggplant-shaped flask, and 10 ml of methanol and 5 ml of 3N hydrochloric acid were added thereto. The mixture was stirred at room temperature for 16 hours. After the dissipation of the peak of the raw material was confirmed by HPLC, the reaction solution was concentrated under reduced pressure to provide a residue. Then, 5 ml of methanol and 690 mg (5.0 mmol) of potassium carbonate were added to the residue and the resulting mixture was agitated at room temperature for 18 hours. The resulting reaction solution was concentrated under reduced pressure, and 20 ml of ethyl acetate and 5 ml of water were added thereto. The resulting mixture was transferred to a separatory funnel and extracted. After the separated organic layer was washed with 5 ml of saturated brine, the separated organic layer was dried with 3 g of magnesium sulfate anhydride, separated by filtration, and concentrated under reduced pressure. The resulting residue was purified by means of silica gel column chromatography (eluent: hexane/ethylacetate=6/1 by volume) to obtain the target compound as a straw-colored, oily substance in an amount of 360 mg (yield: 59.2%). Analytical results on the target compound are given below.

$^1$H-NMR (CDCl$_3$/Me$_4$Si) δ:1.12(t, J=7.1 Hz, 3H), 1.59 (m, 2H), 1.74(m, 2H), 2.12(t, J=6.5 Hz, 2H), 3.37 (m, 2H) 4.06(q, 7.1 Hz), 7.11(m, 2H), 7.31(m, 3H), 9.72(br, 1H)

$^{13}$C-NMR (CDCl$_3$) δ:14.63, 20.02, 22.36, 27.82, 41.39, 58.65, 125.77, 127.73, 128.19, 132.41, 161.18, 170.08

Mass m/z :245 (M+), 198, 173, 143, 115, 105, 82

Example 7

Synthesis of methyl (2S, 2'R)-2-phenyl-2-(2'-piperidinyl)acetate/hydrochloride 10 g (43.3 mmol)of methyl 2-phenyl-2-(2'-piperidinylidene)acetate prepared as in the reference example 1 and 48.45 mg (0.0433 mmol) of [RuI(p-cymene)((R)-H8-BINAP)] were placed in an 50 ml eggplant-shaped flask under a nitrogen atmosphere. To these compounds were added 80 ml of methanol and 24 ml of a hydrochloric acid solution containing 10% methanol. The resultant mixture was transferred into a 100 ml stainless steel autoclave, and the mixture was reacted at 50° C. under a hydrogen pressure of 10 kg/cm$^2$ for 38 hours. The resulting reaction mixture was concentrated under reduced pressure to obtain the target compound in an amount of 11.68 g at a yield of 100%.

150 ml of ethyl acetate and 15 ml of water were added to the 11.8 g of the target compound. The resulting mixture was rendered alkaline by adding 8 ml of a 50% potassium hydroxide solution thereto while the mixture was cooled in an ice bath, whereafter the mixture was extracted using a separating funnel. The resulting organic layer was washed with a saturated brine, dried with magnesium sulfate anhydride, concentrated under reduced pressure, and analyzed by means including HPLC.

In addition, the resulting product was reacted to epimerize the asymmetrical carbon atom at the second position thereof to produce methyl (2R, 2'R)-2-phenyl-2-(2'-piperidinyl)acetate which was analyzed using HPLC.

As a result, the yield of the methyl (2S, 2'R)-2-phenyl-2-(2'-piperidinyl)acetate was 98.7% and the ratio of erythro compound to threo compound was 99:1 in terms of diastereoselectivity. Also, the asymmetrical yield of the erythro compound was 99.4% ee. Analytical results on the target compound are given below.

$^1$H-NMR (D$_2$O) δ: 1.4–1.6 (m, 3.5H), 1.90 (m, 1.5H), 2.13 (m, 1H), 2.99 (m, 1H), 3.31(m ,1H), 3.73 (s, 3H), 3.83 (m, 1H), 3.98 (d, J=9 Hz, 1H), 7.45 (m, 5H)

$^3$C-NMR (D$_2$O) δ:24.03, 24.41, 30.16, 48.31, 55.81, 57.15, 60.69 131.49, 131.95, 132.18, 132.52, 134.72, 175.44

Mass m/z : 234 (M+), 151, 102, 85

Analytical conditions:

High performance liquid chromatography(HPLC) Column: CHIPALPAK AD (Daicel Chemical Industries Co., Ltd.)

Eluent: hexane/isopropanol=98/2 by volume

Flow rate: 0.4 ml/min

Detector: UV=230 nm

Example 8

0.1g (0.43 mmol) of methyl 2-phenyl-2-(2'-piperidinylidene)acetate, 1.5 mg (0.0043 mmol) of [Ir(COD)Cl]$_2$, and 3.7 mg (0.0048 mmol) of BiPh-Ph-BINAP were placed in an 50 ml eggplant-shaped flask under a nitrogen atmosphere. To these compounds were added 2 ml of tetrahydrofuran and the resultant mixture was transferred into a 100 ml stainless steel autoclave, and the mixture was reacted at 100° C. under a hydrogen pressure of 65 kg/cm$^2$ for 18 hours.

The resulting reaction mixture was concentrated under reduced pressure. The resulting residue was analyzed by means of HPLC. As a result, the yield of the methyl 2-phenyl-2-(2'-piperidinyl)acetate was 51.9% and the ratio of an erythro compound to a threo compound was 88:12 in terms of diastereo-selectivity. The asymmetrical yield of the erythro compound was 45.8% ee. Analytical results on the target compound are given below.

¹H-NMR (CDCl₃/Me₄Si) δ:1.4–1.8(m, 6H), 2.50 (dt, J=11 Hz, J=2.9 Hz, 1H), 2.90 (m, 1H), 3.10 (dt, J=10.1 Hz, J=2.2 Hz, 1H), 3.45(d , J=10,1 Hz 1H), 3.65 (s, 3H), , 7.26–7.43 (m, 5H)

¹³C-NMR (CDCl₃) δ:24.48, 25.81, 31.11, 47.06, 51.86, 58.34, 59.02, 127.85, 128.69, 128.87, 136.12, 173.06

Mass m/z : 233 (M+), 150, 118, 84, 54

Example 9

1 g (4.33 mmol) of methyl 2-phenyl-2-(2'-piperidinylidene)acetate and 23.3 mg (0.021 mmol) of [RuI (p-cymene)((R)-BINAP)] were placed in an 50 ml eggplant-shaped flask under nitrogen atmosphere. To these compounds were added 8 ml of methanol and 2.4 ml of a hydrochloric acid solution containing 10% methanol. The resultant mixture was transferred into a 100 ml stainless steel autoclave, and the mixture was reacted at 50° C. under a hydrogen pressure of 40 kg/cm² for 18 hours. The resulting reaction mixture was concentrated under reduced pressure. To the residue thus obtained were added ethyl acetate and an aqueous solution of 50% by weight potassium hydroxide. After extraction, the organic layer generated was dried with magnesium sulfate anhydride, concentrated under reduced pressure, and analyzed by means of HPLC.

As a result, the yield of the methyl 2-phenyl-2-(2'-piperidinyl)acetate was 85.7% and the ratio of erythro compound to threo compound was 97.5:2.5 in terms of diastereoselectivity. The asymmetrical yield of the erythro compound was 88.6% ee.

Examples 10 and 11

The same procedure as in Example 9 was carried out except that the complex for the catalyst was changed to the compounds given in Table 3 and the amount of the complex was 4.33 mmol. The results are shown in Table 3, wherein Ph represents a phenyl group and Me represents a methyl group.

TABLE 3

| Example | Complex | Yield | 5 Threo:Erythro | 6 Threo:Erythro |
|---|---|---|---|---|
| 10 | {Ru₂Cl₄((R)-BINAP)₂}NEt₃ | 75.5 | 0.8:99.2 | 66.6(81.9% ee):33.4 |
| 11 | Ru(OAc)₂((R)-Tol-BINAP) | 79.6 | 2.3:97.7 | 62.1(48.4% ee):37.8 |

Examples 12–14

The same procedure as in Example 9 was carried out except that the ligand of the complex for the catalyst was changed to those given in Table 4 and the amount of the complex was 4.33 mmol. The results are shown in Table 4.

TABLE 4

| Example | Ligand | Yield | 5 Threo:Erythro | 6 Threo:Erythro |
|---|---|---|---|---|
| 12 | (R)-Tol-BINAP | 93.9 | 0.9:99.1 | 73.4(88.8% ee):26.6 |
| 13 | (R)-H8-BINAP | 95.8 | 1.3:98.7 | 58.9(93.4% ee):41.1 |
| 14 | (R)-CMBIPHEMP | 95.2 | 5.4:94.6 (73.2% ee) | 72.2(54.5% ee):27.8 |

Example 15

The same procedure as in Example 3 was carried out except that the solvent and the reaction temperature were changed to those givend in Table 5. The results are shown in Table 5.

TABLE 5

| Example | Solvent | Temperature | yield | 5 Threo:Erythro | 6 Threo:Erythro |
|---|---|---|---|---|---|
| 15 | Methylene chloride | 100° C. | 93.9 | 5.2:94.8 | 76.7(53.0% ee):23.4 |

Examples 16 and 17

The same procedure as in Example 3 was carried out except that the additives and the reaction temperature were changed to those given in Table 6. The results are shown in Table 6.

TABLE 6

| Example | Additive | Temperature | yield | 5 Threo:Erythro | 6 Threo:Erythro |
|---|---|---|---|---|---|
| 16 | Sulfuric acid | 100° C. | 79.8 | 13.4:86.6 | 86.3(2.6% ee):13.7 |
| 17 | Methanol-Hydrochloric acid + Trifluoroacetic acid | 50° C. | 78.9 | 1.8:98.2 | 77.9(92.4% ee):22.1 |

As is clear from the above results, the optically active compound can easily be manufactured by asymmetrically hydrogenating the compound represented by formula (1). The compounds represented by formula (5), among the compounds represented by formula (2), are quite important as a major intermediate for antidepressants.

What is claimed is:

1. A 2-phenyl-2-(2'-piperidinylidene)acetate compound represented by the following formula (1):

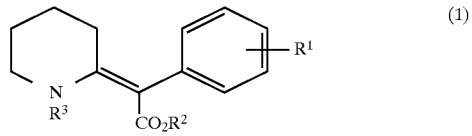

(1)

wherein R¹ represents a hydrogen atom, a lower alkyl group having 1 to 4 carbon atoms, or a lower alkoxy group having 1 to 4 carbon atoms; R² represents a lower alkyl group having 1 to 4 carbon atoms; and R³ represents a hydrogen atom or a protective group for an amino group.

2. A process for manufacturing a 2-phenyl-2-(2'-piperidinylidene)acetate compound represented by the following formula (1):

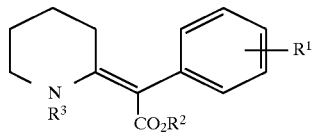 (1)

wherein $R^1$ represents a hydrogen atom, a lower alkyl group having 1 to 4 carbon atoms, or a lower alkoxy group having 1 to 4 carbon atoms; $R^2$ represents a lower alkyl group having 1 to 4 carbon atoms; and $R^3$ represents a hydrogen atom or a protective group for an amino group, which process comprises the step of:

cyclizing a 7-(N-substituted amino)-3-oxo-2-phenyl heptanoate compound represented by the following formula (2):

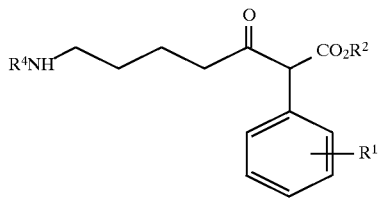 (2)

wherein $R^1$ and $R^2$ are the same groups as defined for formula (1) and $R^4$ represents a protective group for an amino group.

3. A process for manufacturing an optically active 2-phenyl-2- (2'-piperidinyl)acetate compound represented by the following formula (3):

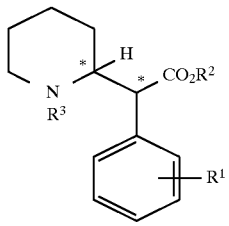 (3)

wherein $R^1$ represents a hydrogen atom, a lower alkyl group having 1 to 4 carbon atoms, or a lower alkoxy group having 1 to 4 carbon atoms; $R^2$ represents a lower alkyl group having 1 to 4 carbon atoms; $R^3$ represents a hydrogen atom or a protective group for an amino group, and * represents an asymmetrical carbon, which process comprises the step of:

asymmetrically hydrogenating a 2-phenyl-2-(2'-piperidinylidene)acetate compound represented by the following formula (1):

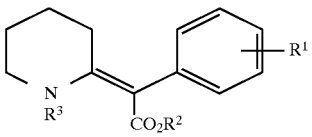 (1)

wherein $R^1$, $R^2$, and $R^3$ are the same groups as defined for formula (3), in the presence of a complex of a Group VIII transition metal.

4. A process as claimed in claim 3, wherein said optically active 2-phenyl-2-(2'-piperidinyl)acetate compound is asymmetrically hydrogenated in the presence of an acid.

5. A process as claimed in claim 4, wherein said acid is selected from a mineral acid.

6. A process as claimed in claim 4, wherein said acid is selected from an organic acid.

7. A process as claimed in claim 3, wherein said complex of the Group VIII transition metal is a complex represented by the following formula (4):

$$M_m L_n X_q Q_r Y_s \qquad (4)$$

wherein M represents a ruthenium atom, iridium atom, or rhodium atom; L represents an optically active phosphine ligand; X represents a hydrogen atom, halogen atom or carboxylic acid derivative residue; Q represents ethylene, 1,5-octadiene, benzene, p-cymene or mesitylene; Y represents an anion selected from the group consisting of $ClO_4^-$, $BF_4^-$, and $PF_6^-$; m, n, and s, respectively, denote an integer of 1 or 2; r denotes an integer of 0 or 1; and q denotes an integer from 0 to 2 or denotes the integer 4.

* * * * *